United States Patent [19]

Borland et al.

[11] Patent Number: 5,107,028
[45] Date of Patent: Apr. 21, 1992

[54] PROCESS FOR TREATING TERT-AMINES

[75] Inventors: James E. Borland; Joe D. Sauer; Kim R. Smith, all of Baton Rouge, La.

[73] Assignee: Ethyl Corporation, Richmond, Va.

[21] Appl. No.: 671,031

[22] Filed: Mar. 18, 1991

[51] Int. Cl.$^5$ .......................................... C07C 209/82
[52] U.S. Cl. .......................................... 564/497; 564/2
[58] Field of Search ............... 564/2, 497; 568/448

[56] References Cited

U.S. PATENT DOCUMENTS

| | | | |
|---|---|---|---|
| 3,567,779 | 3/1971 | Currier et al. | 564/2 |
| 3,742,059 | 6/1973 | Dowd | 564/2 |
| 3,922,306 | 11/1975 | Takaku et al. | 564/497 |
| 4,347,381 | 8/1982 | Tuvell | 564/2 |
| 4,602,108 | 7/1986 | McKinnie | 564/2 |
| 4,766,247 | 8/1988 | Ford et al. | 564/2 |

FOREIGN PATENT DOCUMENTS

| | | | |
|---|---|---|---|
| 95907 | 9/1974 | Japan | 564/497 |
| 1236751 | 10/1986 | Japan | 564/2 |
| 161749 | 7/1987 | Japan | 564/497 |

*Primary Examiner*—Glennon H. Hollrah
*Assistant Examiner*—Shailendra Kumar
*Attorney, Agent, or Firm*—Patricia J. Hogan

[57] ABSTRACT

A tert-amine which contains an acid-activated color body precursor is treated to prevent it or a derivative thereof, e.g., an amine oxide, betaine, or quaternary ammonium compound, from turning pink when exposed to acidic conditions by contacting it with an alkanal containing at least two carbons.

9 Claims, No Drawings

PROCESS FOR TREATING TERT-AMINES

FIELD OF INVENTION

This invention relates to a process for treating a tertamine to prevent pink coloration of the amine or a derivative thereof when exposed to acidic conditions.

BACKGROUND

As disclosed in U.S. Pat. No. 4,347,381 (Tuvell), it is known that some tert-amines and derivatives thereof, e.g., amine oxides, betaines, and quaternary ammonium compounds, are subject to turning pink when exposed to acidic conditions. Neither the pink color body that is formed under acidic conditions nor its acidactivated precursor has yet been identified, and it is not known if the presence of the color body precursor as an impurity in some tert-amines is attributable to the raw materials and/or the techniques used in their syntheses. However, regardless of the primary reason for the discoloration, the pink coloration of the amines and their derivatives is undesirable because of its interference with dyes which are apt to be included in the formulations in which they are used.

A pink tert-amine or derivative thereof can have its color reduced in intensity or even removed by treating it with a bleaching agent, such as hydrogen peroxide, sodium sulfite, sodium bisulfite, sodium thiosulfate, or sodium hypochlorite, as in Tuvell; but it would be preferable to prevent the discoloration from occurring rather than to remove or reduce the discoloration later.

U.S. Pat. No. 3,922,306 (Takaku et al.) teaches that this discoloration of amine salts can sometimes be prevented when the amines are reacted with 0.01-5% by weight of certain borohydrides. According to Takaku et al., the effectiveness of the borohydrides in this regard is unexpected and unique, since it cannot be attained by the use of other reducing agents, such as the sodium sulfite or bisulfite, hydrazine, or hypophosphorous acid of their comparative example. However, it would be desirable to find an alternative to the borohydrides as agents for preventing discoloration of tertamines and derivatives. As indicated by Tuvell, the borohydrides are too expensive to make their use commercially attractive.

SUMMARY OF INVENTION

It has been found that a tert-amine which contains an acid-activated color body precursor can be treated to prevent it or a derivative thereof from turning pink when exposed to acidic conditions by contacting it with an alkanal containing at least two carbons.

DETAILED DESCRIPTION

As is known, the tert-amines which present the aforementioned discoloration problem are amines which contain at least one long-chain alkyl group, and any of these tert-amines can be treated in accordance with the present invention. However, because of their use in preparing derivatives having the greatest commercial interest, the tert-amines which are treated are preferably compounds corresponding to the formula RR'R"N in which R is an alkyl group containing 8-22 carbons; R' is a methyl, ethyl, or hydroxyethyl group; and R" is independently selected from methyl, ethyl, hydroxyethyl, and alkyl groups containing 8-22 carbons.

Of the tert-amines in which R' and R" are independently selected from methyl, ethyl, and hydroxyethyl, those which are of greatest interest are generally the tert-amines in which both R' and R" are methyl; and it is usually also preferred for R' to be methyl in the tertamines wherein R and R" are independently selected from alkyl groups containing 8-22 carbons.

Exemplary of these tert-amines are N-octyldiethylamine, N-octyl-N-hydroxyethylmethylamine, N,N-didecylmethylamine, N-dodecyl-N-tetradecylhydroxyethylamine, N,N-ditetradecylmethylamine, N-tetradecyldimethylamine, N-hexadecyl-N-ethylmethylamine, N-octadecyl-N-eicosylmethylamine, N-docosyldimethylamine, N-tetracosyldimethylamine, and the like.

The alkanal with which the tert-amine is contacted is an alkanal containing at least two carbons From the viewpoint of effectiveness, there does not appear to be any maximum to the number of carbons that the alkanal may contain, but it is generally preferred to use an alkanal containing 2-20 carbons because of cost and availability. Such alkanals include, e.g., ethanal, propanal, $\alpha$-methylpropanal, butanal, $\beta$-methylbutanal, pentanal, hexanal, heptanal, octanal, nonanal, decanal, undecanal, dodecanal, tridecanal, tetradecanal, hexadecanal, octadecanal, and eicosanal.

The amount of alkanal employed is generally at least about 0.1%, based on the weight of the tert-amine, although lesser amounts are effective in at least reducing the discoloration that occurs under acidic conditions and thus can be usefully employed if desired. Since treatment with about 0.1% by weight of the alkanal is usually sufficient to prevent the tert-amine or a derivative thereof from turning pink when exposed to acidic conditions, it is seldom necessary to use a larger amount; but larger amounts can be utilized without deleterious effect. Thus, in most cases, the tert-amine is contacted with about 0.05-5%, preferably about 0.1-1%, most preferably about 0.1-0.5% of the alkanal, based on the weight of the tert-amine.

The treatment of the tert-amine with the alkanal is believed to result in a reaction between the alkanal and the acidactivated color body precursor and a consequent prevention of the formation of a color body when the tert-amine or a derivative thereof is exposed to acidic conditions. This treatment is accomplished by contacting the tert-amine and alkanal in any suitable way, e.g., by dissolving the alkanal in the tert-amine, and then removing the alkanal, e.g., by distillation.

Although the effectiveness of the treatment in preventing later discoloration of the tert-amine is probably at least virtually instantaneous even at room temperature, it is generally desirable to maintain contact between the tert-amine and alkanal for a short time, e.g., 1-30 minutes, to insure that effectiveness. Also, an elevated temperature could be used for the treatment without deleterious effect. However, it is preferred to conduct the treatment at ambient temperatures.

The invention is advantageous as an economical means of treating tert-amines so that neither they nor their derivatives, e.g., amine oxides, betaines, and quaternary ammonium compounds, will turn pink when exposed to acidic conditions.

The following example is given to illustrate the invention and is not intended as a limitation thereof. Unless otherwise specified, quantities mentioned in the example are quantities by weight.

EXAMPLE

Part A - Control

An aliquot of a distilled N-tetradecyldimethylamine was acidified with HCl. Below a pH of 6-7, it developed an intense pink color.

Part B

A 1% solution of decanal in another aliquot of the distilled N-tetradecyldimethylamine of Part A was shaken at room temperature for 15 minutes and then distilled to remove the aldehyde. When treated in this manner and then acidified with HCl as in Part A, the amine remained colorless.

What is claimed is:

1. A process for treating a tert-amine that contains an acid-activated color body precursor so as to prevent pink coloration of the tert-amine or a derivative thereof when exposed to acidic conditions, which process comprises contacting the tertamine with an alkanal containing 2-20 carbons.

2. The process of claim 1 wherein the tert-amine is a compound corresponding to the formula RR'R"N in which R is an alkyl group containing 8-22 carbons; R' is a methyl, ethyl, or hydroxyethyl group; and R" is independently selected from methyl, ethyl, hydroxyethyl, and alkyl groups containing 8-22 carbons.

3. The process of claim wherein R" is methyl, ethyl, or hydroxyethyl.

4. The process of claim 3 wherein R' and R" are methyl.

5. The process of claim 2 wherein R" is an alkyl group containing 8-22 carbons.

6. The process of claim 5 wherein R' is methyl.

7. The process of claim 1 wherein the amount of alkanal is at least about 0.1%, based on the weight of the tert-amine.

8. The process of claim 1 wherein the tert-amine is maintained in contact with the alkanal for 1-30 minutes at ambient temperature.

9. A process for treating a tert-amine that contains an acid-activated color body precursor so as to prevent pink coloration of the tert-amine or a derivative thereof when exposed to acidic conditions, which process comprises contacting the tertamine with decanal.

* * * * *